United States Patent
Kim (10) Patent No.: US 10,004,736 B2
(45) Date of Patent: Jun. 26, 2018

(54) METHOD OF PREVENTING OR TREATING SKIN NECROPTOSIS DISEASE COMPRISING RIP3-MLKL PATHWAY BLOCKER

(71) Applicant: Ajou University Industry-Academic Cooperation Foundation, Gyeonggi-do (KR)

(72) Inventor: You Sun Kim, Gyeonggi-do (KR)

(73) Assignee: Ajou University Industry-Academic Cooperation Foundation, Gyeonggi-do (KR)

( * ) Notice: Subject to any disclaimer, the term of this patent is extended or adjusted under 35 U.S.C. 154(b) by 0 days. days.

(21) Appl. No.: 15/017,470

(22) Filed: Feb. 5, 2016

(65) Prior Publication Data

US 2016/0317535 A1 Nov. 3, 2016

(30) Foreign Application Priority Data

Apr. 30, 2015 (KR) ........................ 10-2015-0061012

(51) Int. Cl.
*A61K 31/506* (2006.01)
*A61K 31/635* (2006.01)
*A61K 38/06* (2006.01)
*A61K 31/45* (2006.01)
*G01N 33/68* (2006.01)
*A61K 45/06* (2006.01)
*A61K 31/4178* (2006.01)

(52) U.S. Cl.
CPC ........ *A61K 31/506* (2013.01); *A61K 31/4178* (2013.01); *A61K 31/45* (2013.01); *A61K 31/635* (2013.01); *A61K 38/06* (2013.01); *A61K 45/06* (2013.01); *G01N 33/6893* (2013.01); *G01N 2333/912* (2013.01); *G01N 2800/20* (2013.01)

(58) Field of Classification Search
None
See application file for complete search history.

(56) References Cited

U.S. PATENT DOCUMENTS

2013/0310424 A1* 11/2013 Surber .................. A61K 9/0078 514/345
2014/0323489 A1* 10/2014 Yuan ..................... C07D 487/04 514/248

OTHER PUBLICATIONS

Li et al., "The B-RafV600E inhibitor dabrafenib selectively inhibits RIP3 and alleviates acetaminophen-induced liver injury", Cell Death and Disease, 2014, e1278, pp. 1-11.*
Lautenschlager, "Cornification disorders—the adequate skin care", Kosmetische Praxis, 2004, pp. 6-8.*
Yuan et al., "Alternative cell death mechanisms in development and beyond", Genes and Development, 2010, pp. 2592-2602.*
Linkermann et al., "Necroptosis", The New England Journal of Medicine, 2014; pp. 455-465.*
Reddy et al., "The Role of Necroptosis in Burn Injury Progression in a Rat Comb Burn Model", Academic Emergency Medicine, 2015, 1181-1186.*
Abe "A novel necroptosis pathway in SJS/TEN", The 39th Annual Meeting of the Taiwanese Dermatological Association, Nov. 16-17, 2013; Session 9: Clinicopathology & Immunology Studies of cADRs; pp. 154-155 (Year: 2013).*
Harr et al. "Toxic epidermal necrolysis and Stevens-Johnson syndrome", Orphanet Journal of Rare Diseases, 2010, pp. 1-11 (Year: 2010).*
Weiss et al. "IL-24 sensitizes tumor cells to TLR3-mediated apoptosis", Cell Death and Differentiation, 2013, pp. 823-833 (Year: 2003).*
Galluzzi et al., "Necroptosis: a specialized pathway of programmed necrosis," Cell (2008) 135(7):1161-1163.
Vanlangenakker et al., "Many stimuli pull the necrotic trigger, an overview," Cell Death Differ (2012) 19(1):75-86.
Kim et al., 2001, *Pan-caspase inhibitor zVAD enhances cell death in RAW246.7 macrophages, Innate Immunity*, 7(4): 292-296.
Moretti et al., 2009, "Radiosensitization of solid tumors by Z-VAD, a pan-caspase inhibitor," *Mol Cancer Ther*, 8(5):1270-1279.
Nussbaum et al., 2004, "The Contraction Phase of Virus-Specific CD8+ T Cells Is Unaffected by a Pan-Caspase Inhibitor," *J Immunol*, 173(11):6611-6618.
Merck Manuals for Stevens-Johnson Syndrome (SJS) and Toxic Epidermal Necrolysis (TEN), available at http://www.merckmanuals.corn/home/skin-disorders/hypersensitivity-and-inflammatory-skin-disorders/stevens-johnson-syndrome-sis-and-toxic-epidermal-necrolysis-ten, accessed Jul. 5, 2017.
Bastuji-Garin et al., 1993, "Clinical classification of cases of toxic epidermal necrolysis, Stevens-Johnson syndrome, and erythema multiforme," *Arch Dermatol*, 129:92-96.

* cited by examiner

*Primary Examiner* — Lianko G Garyu
(74) *Attorney, Agent, or Firm* — Morrison & Foerster LLP (57) ABSTRACT

The present invention relates to methods of preventing or treating skin necroptosis diseases, including administering to subjects receptor-interacting protein kinase-3 (RIP3)-mixed lineage kinase domain-like protein (MLKL) pathway blockers or dabrafenib, and method of diagnosing of skin necroptosis diseases, including detecting phosphorylated MLKL. The RIP3-MLKL pathway blockers according to the present invention directly suppress RIP3 overexpressing in skin necroptosis diseases, or inhibit phosphorylation and translocation to plasma membranes of MLKL, subsequently induced therefrom, thereby effectively preventing skin cell death via necroptosis. Thus, the present invention can prevent or treat a variety of skin diseases caused by necroptosis.

2 Claims, 9 Drawing Sheets
(6 of 9 Drawing Sheet(s) Filed in Color)

METHOD OF PREVENTING OR TREATING SKIN NECROPTOSIS DISEASE COMPRISING RIP3-MLKL PATHWAY BLOCKER

CROSS-REFERENCE TO RELATED APPLICATION

This application claims the priority of Korean Application No. 10-2015-0061012, filed on Apr. 30, 2015. The entire content of this prior application is incorporated herein by this reference.

TECHNICAL FIELD

The present invention relates to methods of preventing or treating skin necroptosis diseases, including administering receptor-interacting protein kinase-3 (RIP3)-mixed lineage kinase domain-like protein (MLKL) pathway blockers or dabrafenib to subjects requiring treatment, and a method of diagnosing of skin necroptosis diseases, including detecting phosphorylated MLKL.

BACKGROUND ART

Most research on cell death focused on apoptosis known as programmed cell death (PCD), and as the enzyme caspase was discovered, many pharmaceutical companies continued to develop drugs using caspase inhibitor for the past 10 years. However, up to now, almost no drugs were approved by the FDA. This is because apoptosis, which refers to cell death occurring in physiological circumstances, is likely to be caused by defense mechanism to retain homeostasis in the body. In contrast, necrosis, which refers to cell death occurring in pathologic circumstances, involves inflammation response in almost all cases. Recent research indicated that diseases caused by necrosis are representatively ischemic (for example, myocardial infarction, stroke, renal infraction), neurodegenerative, and inflammatory diseases (Cell Death and Differentiation (2012) 19, 75-86).

Before the 2000s, cell death was recognized as coming into apoptosis and necrosis. Apoptosis is a representative example of regulated cell death, and necrosis is a representative example of non-regulated cell death. However, recently, a form of cell death, which is different from apoptosis, and also shows morphological characteristics of necrosis, while being regulated by specific proteins, is defined as necroptosis which fuses necrosis and apoptosis. Necroptosis, which refers to programmed necrosis, shows unique characteristics of following programmed cell death mechanism similar to apoptosis, different from necrosis disorderly occurring (Necroptosis: a specialized pathway of programmed necrosis; Cell, Volume 135, Issue 7).

Necroptosis is a non-regulated accidental death form in pathologic circumstances, and its mechanism, molecular target, and signal transduction system have not been studied. Thus, no suitable therapeutic agents for necroptosis diseases have been reported, although it is very urgent to discover and develop substances inhibiting necroptosis, to treat diseases caused by necroptosis and reveal its biological and pathological causes.

Necroptosis diseases, which occur by drugs widely prescribed and used, include drug-induced skin diseases occurring by administration of a substance or drug in an excessive amount or in a wrong manner, or an accurate substance or drug used in an appropriate manner. These diseases are known as incurable diseases since causes thereof are hard to find and no suitable therapeutic agents are developed. Particularly, according to the Korean Society for Pharmacoepidemiology and Risk Management, it is known that about 1,700 distributed pharmaceuticals induce drug-induced skin diseases, representatively, Stevens-Johnson syndrome or toxic epidermal necrolysis. Thus, it is very urgent to develop a novel therapeutic agent and method of preventing or treating these diseases.

SUMMARY OF INVENTION

The present inventors completed the present invention after confirming that the pathway leading from receptor-interacting protein kinase-3 (RIP3) to mixed lineage kinase domain-like protein (MLKL) induces diseases associated with necroptosis which is different from apoptosis, and that when blocking the RIP3-MLKL pathway, skin necroptosis diseases can be effectively treated.

It is an object of the present invention to provide a method of preventing or treating a skin necroptosis disease, including administering an RIP3-MLKL pathway blocker to a subject requiring treatment. Particularly, it is an object of the present invention to provide a method of preventing or treating a skin necroptosis disease, including administering dabrafenib to a subject requiring treatment.

Also, it is an object of the present invention to provide a method of diagnosing of a skin necroptosis disease, including detecting phosphorylated MLKL.

In order to achieve the above objects, the present invention provides a method of preventing or treating a skin necroptosis disease, including administering a RIP3-MLKL pathway blocker to a subject requiring treatment.

Also, the present invention provides a method of preventing or treating a skin necroptosis disease, including administering dabrafenib to a subject requiring treatment.

Also, the present invention provides a method of diagnosing of a skin necroptosis disease, including detecting the overexpression of RIP3-MLKL or phosphorylated MLKL.

The RIP3-MLKL pathway blocker according to the present invention, for example, dabrafenib, can directly suppress RIP3 overexpressing in skin necroptosis diseases or inhibit phosphorylation and translocation of MLKL to plasma membranes, subsequently induced therefrom, thereby effectively preventing skin cell death by necroptosis. Thus, the present invention has excellent effects of preventing or treating a variety of skin necroptosis diseases in which cell death occurs by necroptosis.

BRIEF DESCRIPTION OF DRAWINGS

The patent or application file contains at least one drawing executed in color. Copies of this patent or patent application publication with color drawing(s) will be provided by the Office upon request and payment of the necessary fee.

In FIG. 1B, HR stands for heart rate, BUN stands for blood urea nitrogen, BAS stands for body surface area, ESR stands for erythrocyte sedimentation rate, CRP stands for C-reactive protein, and PA/EA stands for pigmented area per measured epidermal area.

DETAILED DESCRIPTION FOR CARRYING OUT THE INVENTION

The present invention provides a method of preventing or treating a skin necroptosis disease, including administering a receptor-interacting protein kinase-3 (RIP3)-mixed lineage kinase domain-like protein (MLKL) pathway blocker to a subject requiring treatment.

Also, the present invention provides a composition for preventing or treating a skin necroptosis disease including an RIP3-MLKL pathway blocker.

The RIP3-MLKL pathway blocker according to the present invention directly suppresses RIP3 overexpressing in skin necroptosis diseases or inhibits MLKL phosphorylation and translocation to plasma membranes, subsequently induced therefrom, thereby effectively preventing cell death via necroptosis. Thus, the present invention has excellent effects of preventing or treating a variety of skin necroptosis diseases in which cell death occurs by necroptosis.

As used herein, the term "RIP3-MLKL pathway blocker" refers to a substance blocking a signal transduction pathway leading from RIP3 to MLKL, consequently to a substance capable of blocking, inhibiting, or alleviating programmed necrosis, i.e., necroptosis. RIP3 is a significant part of cellular mechanisms of inflammation and necroptosis occurring in epidermal keratinocytes under specific conditions. A key lower pathway of RIP3, downstream of RIP3, is MLKL. Although significant difference is not observed in skin lesions of TEN, compared to normal skin, elevated MLKL phosphorylation is observed in skin lesions of TEN, different from normal skin.

The pathway blocker may unlimitedly include substances blocking all pathways associated with necroptosis, i.e., programed necrosis, occurring when RIP3 and MLKL are involved, including substances blocking RIP3 phosphorylation, MLKL phosphorylation by phosphorylated RIP3, translocation of phosphorylated MLKL to plasma membranes, reactive oxygen species (ROS) caused by RIP3-MLKL, or JNK and p38 activation generated from ROS.

Preferably, the RIP3-MLKL pathway blocker may be an RIP3 inhibitor or an MLKL inhibitor. More preferably, the inhibitor may include at least one activation inhibitor selected from the group consisting of or a compound, a peptide, a peptide mimetic, a substrate analogue, an aptamer, and an antibody, specifically binding to a protein promoting the activation of RIP3 or MLKL, RIP3 or MLKL, or a substance capable of inhibiting gene expression of RIP3 or MLKL, as one selected from the group consisting of antisense nucleotide, siRNA, shRNA, and a ribozyme, complementarily binding to mRNA of gene promoting RIP3 or MLKL expression. More preferably, the RIP3 inhibitor is a knockdown substance of RIP3, for example, necrostatin-1, or dabrafenib, which is an RIP3 inhibitor, and the MLKL inhibitor is necrosulfonamide.

The RIP3-MLKL pathway blocker according to the present invention excellently blocks the RIP3-MLKL pathway, and thus can be useful in preventing or treating a skin necroptosis disease.

As used herein, the term "skin necroptosis disease" refers to a skin disease caused by cell death which is different from apoptosis and necrosis. Programmed necrosis, i.e., necroptosis, is activated in response to death receptor ligands and other cellular stressors. Cell death via necroptosis, programmed or regulated cell death, is different from apoptosis in that caspases are not involved in cell death, but that membrane permeability increases and destruction by cell lysis is induced. Further, cell death via necroptosis, which is programmed and regulated, is different from necrosis, which disorderly occurs.

Necroptosis includes the formation of necrosome or ripoptosome containing receptor-interacting protein kinases RIP3 (RIPK3) and RIPK1 and recruitment of MLKL. RIP3- dependent phosphorylation and plasma membrane localization of phosphorylated MLKL is necessary for necroptosis, and induces skin necroptosis diseases.

The skin necroptosis disease may be at least one selected from the group consisting of drug-induced cell death, burns, frostbite, erythema multiforme, skin diseases caused by bacterial or viral infection, pityriasis lichenoides et varioliformis acuta, lupus erythematosus, and lichen planus. Particularly, the drug-induced cell death may be at least one selected from the group consisting of drug eruption, Stevens-Johnson syndrome/toxic epidermal necrolysis (SJS/TEN), and angiodermatitis.

Thus, the present invention provides a method of preventing or treating a skin necroptosis disease, wherein the skin necroptosis disease is at least one selected from the group consisting of drug-induced cell death, burns, frostbite, erythema multiforme, skin diseases caused by bacterial or viral infection, pityriasis lichenoides et varioliformis acuta, lupus erythematosus, and lichen planus.

The drug-induced cell death, which refers to a disease caused by a drug widely prescribed and used, is cell death via necroptosis by various causes occurring by administration of a substance or drug used in an excessive amount or in a wrong manner, or an accurate substance or drug used in an appropriate manner. The disease that may occur by the drug-induced cell death may be, but not limited to, one selected from the group consisting of drug eruption, SJS/TEN, and angiodermatitis.

Thus, the present invention provides a method of preventing or treating a skin necroptosis disease, wherein the drug-induced cell death is one selected from the group consisting of drug eruption, SJS/TEN, and angiodermatitis.

SJS/TEN, which is a disease where a rash arises on face, neck, jaw, etc., in early stage, and then erythema, necrosis, and bullae all over the body, is caused mainly by a drug and involves acute severe mucous membrane reactions. SJS involves skin detachment of 10% or less of the entire body surface area, and TEN involves skin detachment of 30% or more of the entire body surface area.

SJS/TEN is known to be caused mainly by a drug, including sulfonamide, cotrimoxazole, ampicillin, and macrolide, which are antibiotics, phenytoin, carbamazepine, phenobarbital, and lamotrigine, which are anticonvulsants, oxicam, which is a type of anti-inflammatory analgesic drug, and allopurinol, which is a uric acid lowering drug.

Also, the RIP3-MLKL pathway blocker of the present invention may be administered in combination with a substance that can be used in preventing or treating skin necroptosis and a disease associated therewith.

The substance that can be used in preventing or treating skin necroptosis and a disease associated therewith may be at least one selected from the group consisting of, for example, an anticancer drug, an antiviral drug, an antibiotic, an anti-inflammatory drug, an anticoagulant, a lipid metabolism improver, a cell death inhibitor, an antihypertensive drug, a therapeutic agent for diabetes/obesity, a therapeutic agent for a cardiovascular disease, a therapeutic agent for a degenerative neuronal disease, an antiaging agent, and a therapeutic agent for a metabolic disease.

Particularly, the present invention provides a pharmaceutical composition for preventing or treating a cell necroptosis disease further including zVAD, cyclohexamide, or a second mitochondrial derived activator of caspases (SMAC) mimetic.

The present invention provides a method of preventing or treating a cell necroptosis disease, including administering a pharmaceutical composition further including zVAD, cyclohexamide, or a SMAC mimetic to a subject requiring treatment.

The pharmaceutical composition of the present invention may include an additional ingredient capable of being used for preventing or treating a skin disease associated with cell necroptosis or that may be caused by apoptosis, or simultaneously or subsequently with the use of the additional ingredient.

Also, the present invention provides a pharmaceutical composition for preventing or treating SJS/TEN including dabrafenib.

Also, the present invention provides a method of preventing or treating SJS/TEN, including administering dabrafenib to a subject requiring treatment.

The dabrafenib, which is known as an anticancer drug, can inhibit RIP3-mediated MLKL phosphorylation by acting as an RIP3 inhibitor capable of inhibiting kinase activity of RIP3 in the RIP3-MLKL pathway, and thus may effectively inhibit cell necroptosis occurring in skin cells.

Thus, dabrafenib of the present invention may be used as a novel therapeutic agent for SJS/TEN caused by necroptosis by effectively inhibiting skin cell necroptosis through inhibition of RIP3-mediated MLKL phosphorylation.

The composition of the present invention includes a pharmaceutically acceptable carrier. The pharmaceutically acceptable carrier included in the pharmaceutical composition of the present invention, which is generally used in formulating the composition, may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propylhydroxy benzoate, talc, magnesium stearate, mineral oil, saline solution, phosphate buffered saline (PBS), or a medium, but is not limited thereto.

In addition to the above ingredients, the pharmaceutical composition according to the present invention may further include a lubricant, a humectant, a sweetener, a fragrant, an emulsifying agent, a suspending agent, a preservative, etc.

The pharmaceutical composition according to the present invention may be administered orally or parenterally, preferably orally.

An appropriate dosage of the pharmaceutical composition of the present invention may vary depending on a variety of factors including the method of formulation, the mode of administration, the patient's age, weight, and gender, pathological condition, diet, the time of administration, the route of administration, excretion rate, response sensitivity, and the like.

The subject for administration in the present invention is preferably mammals including humans, and includes patients who have undergone, is undergoing or may potentially undergo skin necroptosis, without limitation. The RIP3-MLKL pathway blocker may be delivered to the subject in a pharmaceutically effective amount.

Also, the present invention provides method of diagnosing of a skin necroptosis disease, including detecting the overexpression of RIP3-MLKL or phosphorylated MLKL.

Also, the present invention may provide guidelines on an effective treatment method according to the method of diagnosing of a disease of the present invention.

In a patient suffering from a skin necroptosis disease, the amount of MLKL does not increase, but phosphorylation of MLKL may be strongly induced by an increase in its upstream regulator RIP3. Thus, when the phosphorylation of phosphorylated MLKL is detected in a diagnosis sample, the information on whether the subject patient has a skin necroptosis disease may be provided more quickly and effectively, and the information that can effectively treat the disease through drug administration targeting the disease may be provided.

The detection of phosphorylated MLKL may be performed without limitation through a technique disclosed in the art which can identify the level of phosphorylation of a substance. Further, it can be determined whether the detected sample belongs to a patient with a skin necroptosis disease through comparison with phosphorylated MLKL of a normal level. From this, a possibility to select a therapeutic agent is suggested and guidelines on effective treatment may be provided.

Hereinafter, the present invention is described in detail with reference to preparation examples and examples. The following preparation examples and the examples are provided for illustrative purposes only, and those skilled in the art will appreciate that the present invention is not limited to the scope of the preparation examples and the examples.

Immunohistochemistry and Image Analysis 3 mm of skin biopsy specimens were obtained from 10 toxic epidermal necrolysis (TEN) patients. Normal skin tissues were obtained from 5 patients who had done skin biopsy for diagnosis of pigmentary disease as controls. Paraffin-embedded tissue sections with 3 μm thickness were processed for optical microscopic examination. Immunohistochemistry was performed by standard techniques using primary antibodies to RIP3, MLKL, and p-MLKL. Quantitative analysis of immunohistochemistry was done using Image Pro Plus, Version 4.5. The ratio of pigmented area per the measured epidermal area (PA/EA) was measured in normal skin and TEN skin lesions.

Cell Culture

All cells were cultured in primary human dermal fibroblasts at 37° C. in 5% $CO_2$. Fibroblasts and HaCaT cells were cultured in DMEM supplemented with 10% PBS, 2 mM glutamine, 100 U/mL penicillin and 100 μg/mL streptomycin. Primary normal human KC was cultured by a technique disclosed in the art. Skin specimens were obtained from repeat Caesarean section deliveries and grown in Epilife medium with human keratinocyte growth supplement. Cells at passage 3-10 were used for experiments. Human neonatal epidermal keratinocyte (HEKn) were obtained from Gibco and maintained according to the manufacturer's instructions, and they were used for experiments.

Statistics

Independent experiments were performed at least in triplicate. Statistical significance was evaluated in paired analyses using the Mann-Whitney U test (nonparametric). Data values are expressed as mean±SEM. Statistical significance was considered $p<0.05$.

Example 1. Confirmation on Increased RIP3 Expression in TEN Lesions

It was examined whether RIP3 protein expression increases in skin tissues obtained from TEN patients with noticeable epidermal keratinocyte cell death. The experiment on TEN patients was approved by IRB MED-KSP-13-029. FIG. 1A-E show a state image of TEN patients' skin used and clinical and laboratory experimental results observed from 10 TEN patients.

Figure 1A:
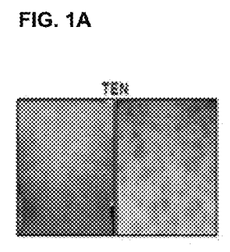
FIG. 1A-E show clinical observation of TEN patients' skin (FIG. 1A), clinical characteristics and laboratory results for TEN patients, and association between CRP levels elevated in response to inflammatory response and RIP3 expression (FIGS. 1C and 1D), and expression levels of MLKL, which is a protein whose activation is regulated by RIP3 (FIG. 1E).
Figure 1B:
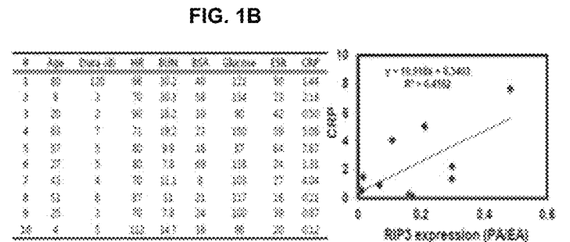
Figure 1C:
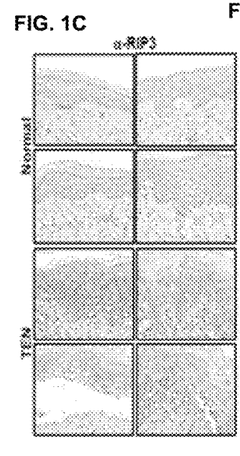
Figure 1D:
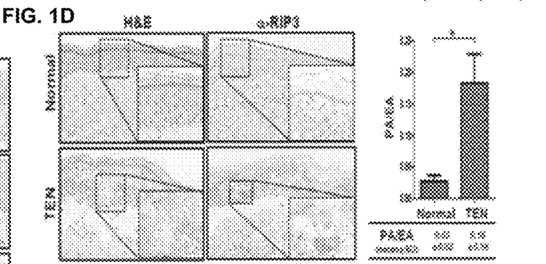
Figure 1E:
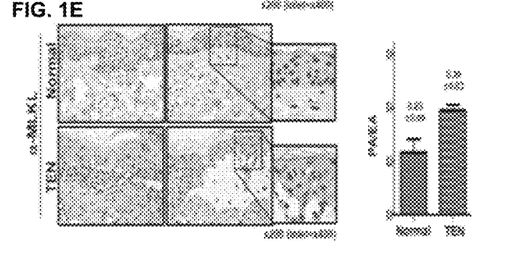

As shown in FIG. 1A-E, it was confirmed that bullae, epidermal detachment, and multiple erythematous macules were observed in the TEN patients' skin (FIG. 1A), and that C-reactive protein (CRP) levels rapidly rose in response to inflammation. Further, it was shown that the CRP levels were positively correlated with RIP3 expression in the skin lesions of TEN patients, as measured by IHC (FIG. 1B). Immunohistochemical staining and H & E staining were used to compare RIP3 expression and skin lesions between TEN patients and normal skin. In TEN skin, TEN skin lesions with eosinophilic epidermal necrosis and separation of dermo-epidermal junction were observed, whereas in normal skin with no skin lesions by TEN, no abnormalities were observed (FIG. 1D). When compared to normal skin, relative IHC sections showed a significant increase in RIP3 expression levels in TEN skin. As a result of quantification using an image analysis program, it was confirmed again that RIP3 expression in the epidermal area (PA/EA) was significantly increased in the TEN skin compared to normal skin (FIGS. 1C and 1D). In contrast to RIP3, expression of MLKL, the downstream effector, was not statistically different in TEN skin compared to normal skin (FIG. 1E).

The above result indicates that RIP3 overexpresses in TEN skin compared to normal skin, and that RIP3 may be a target as a significant regulator of necroptosis.

Example 2. Confirmation on Association Between Necroptosis and RIP3

From Example 1, it was confirmed that the overexpression of RIP3 in TEN patients with necroptosis may be a significant target. Thus, it was examined whether various types of skin cells including primary melanocytes, fibroblasts, and keratinocytes, expressing RIP3 may execute necroptosis, which is programmed necrosis.

The immortal human keratinocyte line HaCaT and primary human epidermal keratinocyte isolated from neonatal foreskin (HEKn) responded to prototypical necroptosis stimuli induced by TNFα (TNFα□+zVAD+cyclohexamide or SMAC mimetic; also referred to herein as TCZ or TSZ). Inhibition of caspase activity by zVAD completely blocked caspase-3 and PARP processing, but did not prevent TNF-induced cell death. This result indicates that RIP3-expressing keratinocytes die by prototypical programmed necrosis, necroptosis, not by apoptosis due to caspase activity. This result is similar to that observed in HT-29 cell line, which is a standard model for study of necroptosis. Additionally, from a knockout model, it was confirmed whether RIP3 and RIP1 affect TNF-induced cell death via necroptosis. The result is shown in FIGS. 2A and 2B.

Figure 2A:
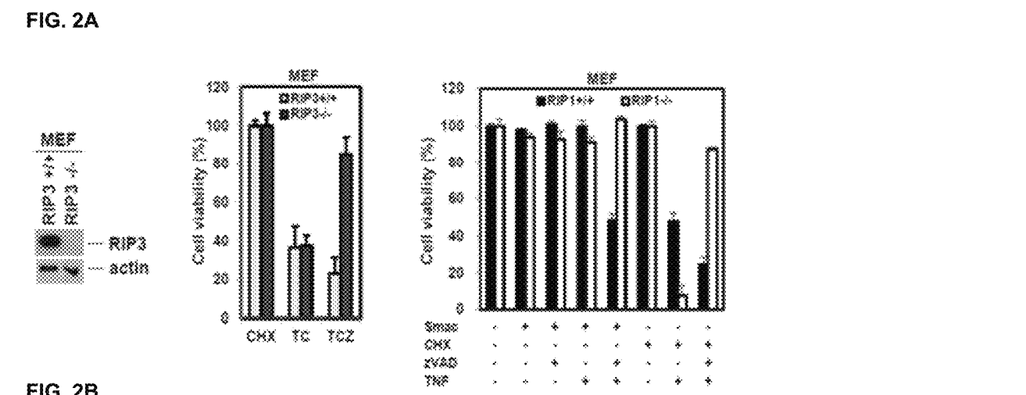
FIG. 2A shows a result confirming cell viability by CHX, TC, and TCZ treatment in MEF cells where RIP3 or RIP1 was knocked out.

As shown in FIG. 2A, it was confirmed that RIP3 and RIP1 knockout MEF cells were resistant to TNF-induced cell death via necroptosis, which is consistent with the roles of these proteins in necroptosis progress.

Figure 2B:
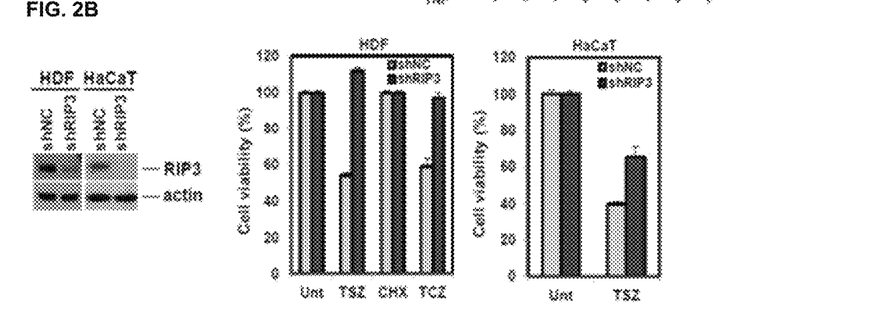
FIG. 2B shows a result confirming cell death inhibition effect by TCZ, TSZ, and CHX treatment in HDF and HaCaT cells where RIP3 was knocked down (shRIP3). Herein, CHX refers to cyclohexamide, TCZ stands for TNF-α+cyclohexamide+zVAD, and TSZ stands for TNF-α+SMAC mimetic+zVAD.

Similarly, as shown in FIG. 2B, it was confirmed that TNF-induced cell death via necroptosis was effectively reduced in human dermal fibroblasts in RIP3 knockdown shRIP3 experimental group. This result demonstrates that particularly RIP3 is significantly associated with skin cell necroptosis.

Example 3. Effect of RIP3 Inhibitor on Necrosis Inhibition

It is known that lesional skin of TEN patients is characterized by exhibiting high levels of iNOS and is associated with NO production. It is expected that induction of RIP3 occurs upstream and independently of NO production in TEN, since sodium nitroprusside (SNP), a model agent of NO donor, does not induce RIP3 (or TNFα) expression. In order to identify the association between SNP and RIP3 observed in TEN, HaCaT and HEKn cells expressing RIP3 were treated with 0 to 5 mM SNP for 24 hours, and cell viability and phosphorylation of relevant factors were analyzed by MTT assay and western blotting.

Figure 3A:
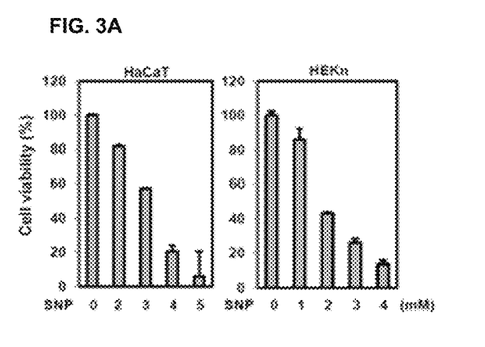
FIGS. 3A and 3B show a result confirming a change in MAPK phosphorylation according to SNP treatment in HaCaT and HEKn cells.
Figure 3B:
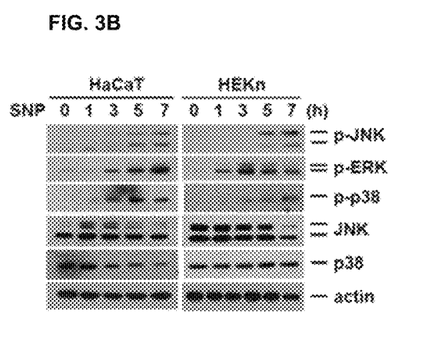

As shown in FIGS. 3A and 3B, SNP treatment to both cells induced dose-dependent necrotic cell death (FIG. 3A), and phosphorylation of MAPK over the treatment time (FIG. 3B).

Similar to the result confirmed in Example 2, the pan-caspase inhibitor zVAD did not significantly affect SNP-induced cell death, but completely blocked caspase-3 and PARP cleavage induced by TNF/CHX and SNP.

Whether SNP-induced cell death is improved by RIP1 and necrostatin-1 (Nec-1), and combination treatment of zVAD and Nec-1 was examined in HaCaT cells using MTT assay and phase-contrast microscopy. Cells were pretreated with 80 μM of Nec-1 and/or 20 μM of zVAD for 1 hour, followed by SNP treatment. The result of cell viability is shown in FIG. 4.

Figure 4:
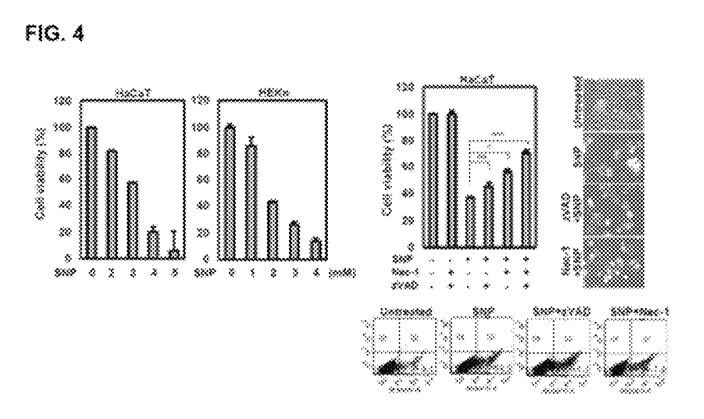
FIG. 4 shows a result confirming cell death inhibition effect by SNP, necrostatin-1 (Nec-1), and zVAD treatment in HaCaT cells.

As shown in FIG. 4, it was confirmed that SNP-induced cell death was reduced by pretreatment with Nec-1 and zVAD, and that SNP-induced cell death was more remarkably inhibited in the experimental group treated with a combination of zVAD and Nec-1, rather than with zVAD alone. Phase-contrast microscopy and Annexin-V staining indicated that SNP-induced cell death was inhibited by treatment with compounds such as Nec-1.

Based on the above result, further examination was conducted on the effect of dabrafenib on necroptosis inhibition, which inhibits RIP3 kinase activity, and necrosulfonamide (NSA), which inhibits MLKL functions downstream of RIP3 phosphorylation. The result is shown in FIG. 5.

Figure 5:
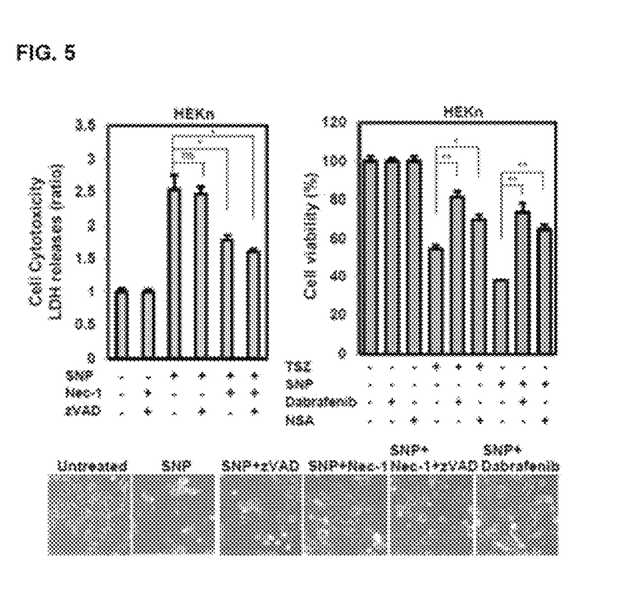
FIG. 5 shows a result confirming cell death inhibition effect by SNP, Nec-1, zVAD, TSZ, dabrafenib, and necrosulfonamide (NSA) treatment in HEKn cells.

As shown in FIG. 5, it was confirmed that treatment with all Nec-1, dabrafenib, and NSA protected HEKn cells from acute SNP cytotoxicity more effectively than zVAD. This result indicates that SNP-induced cell death is inhibited partially by the pan-caspase inhibitor zVAD, but more effectively by Nec-1, dabrafenib, and NSA, targeting RIP3. It was confirmed that cell necroptosis in TEN patients was not completely inhibited by the mechanism of zVAD which inhibits TNF-induced cell death, but was effectively inhibited when targeting RIP3.

Example 4. Confirmation on Effect of RIP3 Knockdown on SNP-Induced Cell Death Inhibition In order to further confirm the association between RIP3 and SNP-induced cell death, whether RIP3 knockdown affects SNP-induced cell death was examined. RIP3 knockdown was indicated as shRIP3, and HaCaT cells having shRIP3 were treated with SNP for 24 hours and cell viability was evaluated using MTT assay and phase-contrast microscopy. Further, HEKn cells having shRIP3 were treated with SNP or TSZ for 24 hours and the same analysis was conducted, and cell lysates were analyzed over SNP treatment time by western blotting. The result is shown in FIGS. 6A and 6B.

Figure 6A:
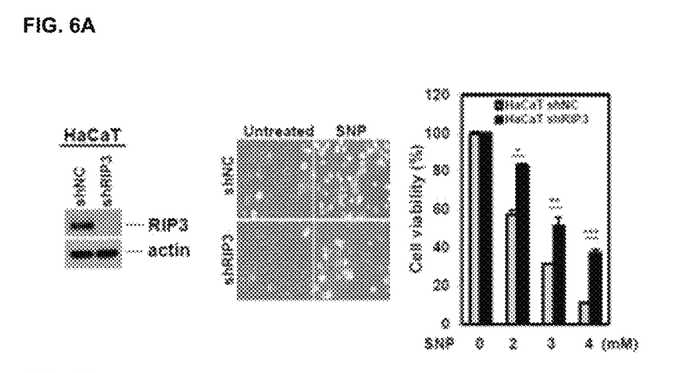
FIGS. 6A and 6B show a result confirming cell death inhibition effect after treating SNP to RIP3 knockdown shRIP3 HaCaT (FIG. 6A) and HEKn (FIG. 6B).
Figure 6B:
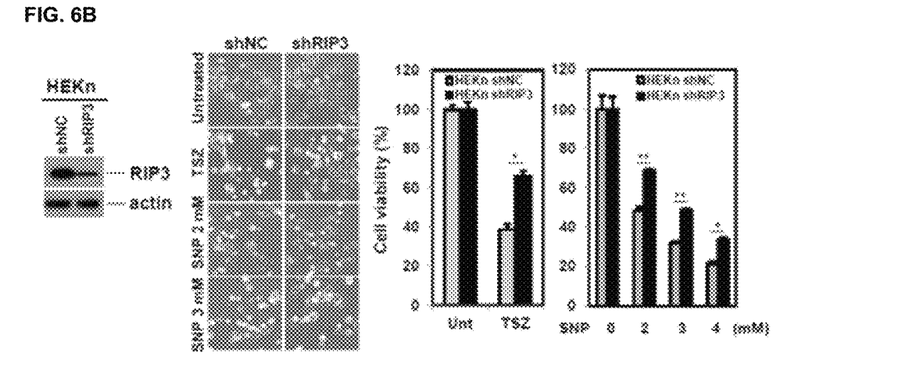

As shown in FIGS. 6A and 6B, in shRIP3 experimental group where RIP3 was knocked down in HaCaT and HEKn cells, no RIP3 was expressed and cell death induced by SNP treatment was significantly inhibited in every SNP treatment concentration, compared to cells normally expressing RIP3.

Sustained activation of the stress kinases JNK and p38 is considered often associated with necroptosis, and is known to be essential for cell death in some cell types. In this regard, in order to confirm whether SNP-induced JNK and p38 activation is inhibited in RIP3 knockdown cells to inhibit necrosis, cell lysates treated with SNP were analyzed over treatment time by western blotting, and the change in p-JNK, p-38, and p-ERK expressions in RIP3 knockdown cells was analyzed. The result is shown in FIG. 7.

Figure 7:
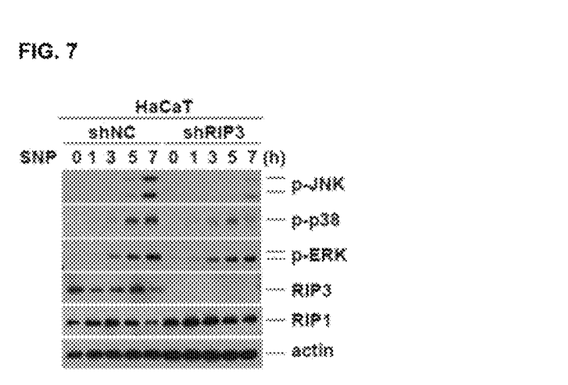
FIG. 7 shows a result confirming activation inhibition effect of SNP-induced stress kinases after treating SNP to RIP3 knockdown shRIP3 HaCaT (a) and HEKn (b).

As shown in FIG. 7, SNP-induced JNK and p38 activation was significantly inhibited in RIP3 knockdown cells, shRIP3. This result indicates that the inhibition of the RIP3-MLKL pathway leads to inhibition of activation of the stress kinases such as JNK and p38, to inhibit cell necroptosis.

Example 5. Confirmation on Association Between RIP3 Overexpression and SNP-Induced Cell Death In order to confirm the function of overexpressed RIP3, since RIP3 was overexpressed in TEN patients, RIP3 was ectopically expressed in HaCaT and HEKn cells, to evaluate the sensitivity of cells to SNP. To induce ectopic RIP3 expression, HaCaT or HEKn cells were infected with pLX303-hRIP lentiviral plasmid, and cells at passage 3-6 were used for experiments. Specifically, short-hairpin RNA (shRNA) plasmids targeting hRIP3 mRNA (NM_006871) were purchased from Sigma-Aldrich. Lentiviral plasmids were transfected into 293TN cells. Pseudoviral particles were collected 2 days after the transfection, and infected into cells with 10 μg/mL of polybrene. Infected cells were puromycin-selected 2 days after infection. Whether HaCaT and HEKn cells infected with pLX303-hRIP lentiviral plasmid stably overexpress RIP3 was examined using western blotting and immunohistochemistry. The result is shown in FIGS. 8A and 8B.

Figure 8A:
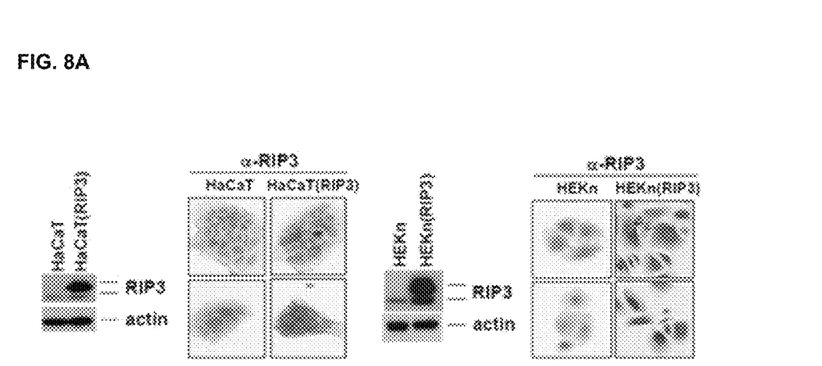
FIGS. 8A and 8B show a result confirming RIP3-overexpressing HaCaT and HEKn cells (FIG. 8A), and SNP sensitivity according to SNP treatment (FIG. 8B).
Figure 8B:
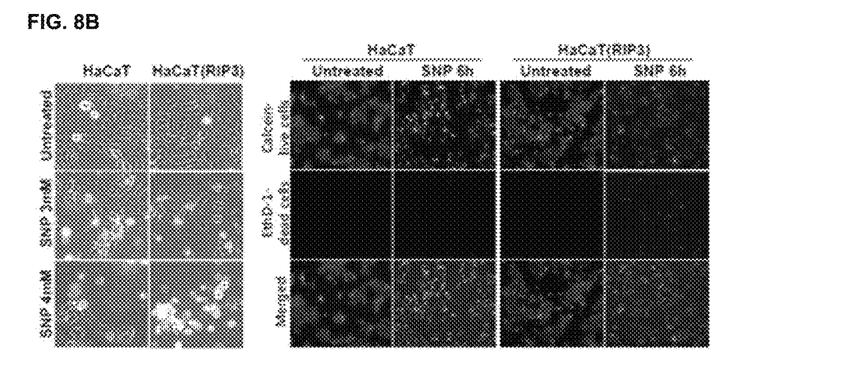

As shown in FIGS. 8A and 8B, it was confirmed that all infected cells overexpress RIP3, compared to non-treated cells (FIG. 8A). 5 mM of SNP was treated for 6 hours, and it was analyzed by Calcein/EthD-1 live/death assay that cells overexpressing RIP3 is more sensitive to SNP (FIG. 8B). The result indicates that overexpressed RIP3 plays a significant role in increasing SNP sensitivity. Since SNP induces necroptosis in TEN patients, RIP3 overexpression increases the sensitivity to SNP which is a nectrotic stimulus, thereby reinforcing necroptosis progress.

The sustained JNK activation and induction of ROS are associated with cell death via necroptosis. Thus, whether activation of JNK and p38 by SNP was promoted by RIP3 overexpression, cells treated with 5 mM of SNP for 0 to 7 hours were analyzed using western blotting of p-JNK and p-38. The result is shown in FIG. 9.

Figure 9:
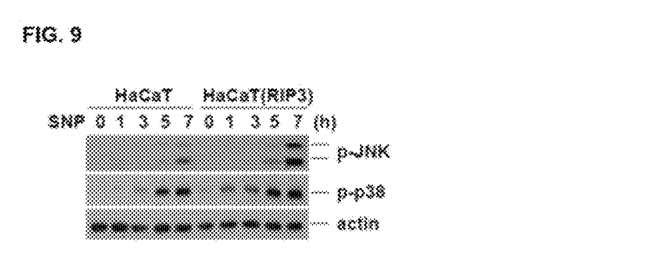
FIG. 9 shows a result of confirming activation promotion effect of SNP-induced stress kinases in RIP3-overexpressing HaCaT cells.

As shown in FIG. 9, it was confirmed that RIP3 overexpression had no effect on TNFα-induced MAP kinase activity, but that RIP3 overexpression promoted activation of JNK and p38 by SNP. As ROS inactivates JNK phosphates, leading to JNK activation, the change in ROS production by SNP treatment was additionally measured. Cells were treated with 5 mM of SNP for 5 hours, and ROS production (DCFH-DA) was measured by FACS and visualized by fluorescence microscopy. The result is shown in FIG. 10.

Figure 10:
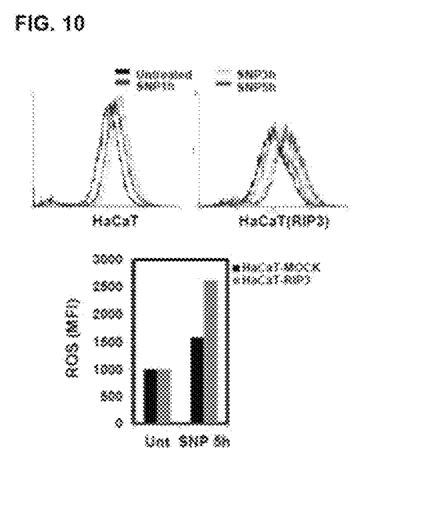
FIG. 10 shows a result confirming SNP-induced ROS production promotion effect in RIP3-overexpressing HaCaT cells. Herein, ROS stands for reactive oxygen species.

As shown in FIG. 10, ROS production rapidly increased in HaCaT cells overexpressing RIP3. The result indicates that high expression of RIP3 is associated with ROS production and promotes ROS production, thereby reinforcing JNK activation and promoting SNP-induced cell necroptosis.

Figure 11A:
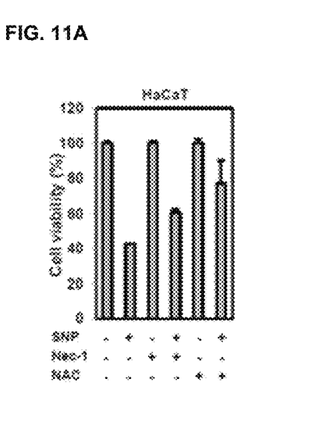
FIG. 11A shows a result confirming SNP-induced cell death inhibition effect by NAC pretreatment and Nec-1 treatment.
Figure 11B:
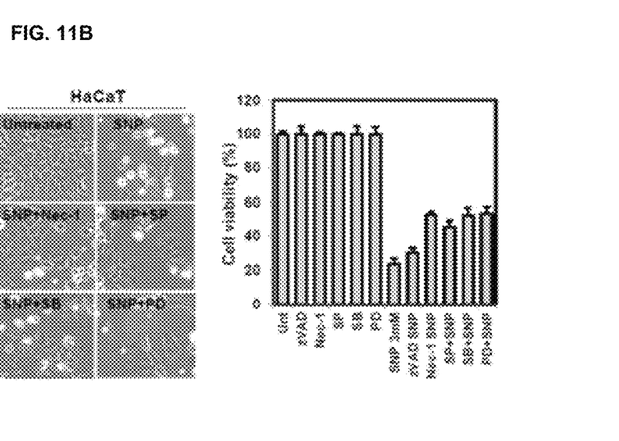
FIG. 11B shows a result confirming that SNP-induced cell death is inhibited by treatment with JNK inhibitor SP420119 (SP), p38 inhibitor sB202190 (SB), and MEK, ERK upstream, inhibitor PD98059 (PD).

However, as shown in FIGS. 11A and 11B, in cells pretreated with NAC having ROS scavenging ability, SNP-induced cell death was inhibited similarly in Nec-1 treated group (FIG. 11A). From this, it was confirmed again that ROS is associated with SNP-induced cell death. Further, SNP-induced cell death was inhibited by treatment with JNK inhibitor SP420119 (SP), p38 inhibitor sB202190 (SB), and MEK, upstream of ERK, inhibitor PD98059 (PD) (FIG. 11B). This result indicates that an increase in RIP3 induced an increase in ROS production, which activates JNK and p38, thereby eventually promoting cell death.

Example 6. Association Between RIP3 and MLKL in Cell Death Via Necroptosis

RIP3-dependent phosphorylation and translocation to plasma membrane of MLKL are known to be essential for programmed necrotic cell death, necroptosis. Experiments were conducted in order to identify the association between MLKL phosphorylation and RIP3 expression by SNP treatment.

First, in order to confirm whether SNP treatment induces MLKL phosphorylation in cells, HEKn cells were treated with SNP for 7 hours and lysates of HEKn cells were analyzed by western blotting at each time point. Further, confocal immunofluorescence pictures were used to examine phosphorylated MLKL in HEKn cells treated with TSZ and 5 mM of SNP for 6 hours. The result is shown in FIG. 12.

Figure 12:
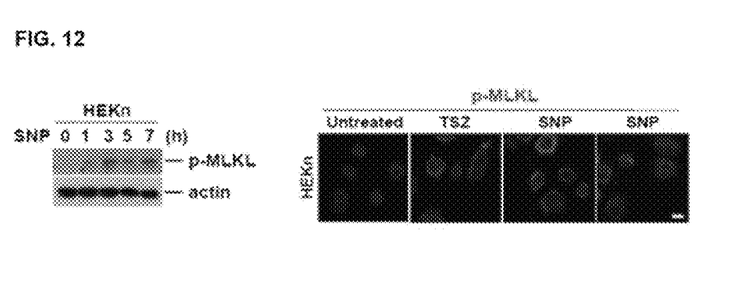
FIG. 12 shows a result confirming MLKL phosphorylation and p-MLKL translocation to plasma membranes by SNP treatment in HEKn cells.

As shown in FIG. 12, it was confirmed that p-MLKL increased by SNP treatment over time, and that translocation of SNP-induced p-MLKL to plasma membrane showed the pattern similar to that seen with TSZ treatment.

Thereafter, in order to confirm whether high expression of RIP3 is associated with MLKL activation and cell death by necroptosis, shRIP3-HEKn cells were treated with 5 mM of SNP, and cell lysates were analyzed by western blotting. Also, the association between RIP3 overexpression and p-MLKL was analyzed in parental and RIP3-overexpressing HaCaT/HEKn cells. The result is shown in FIGS. 13A and 13B.

Figure 13A:
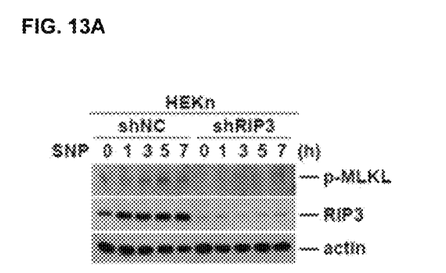
FIG. 13A shows a result confirming MLKL phosphorylation inhibition effect by SNP treatment in RIP3 knockdown shRIP3 HEKn cells.
Figure 13B:
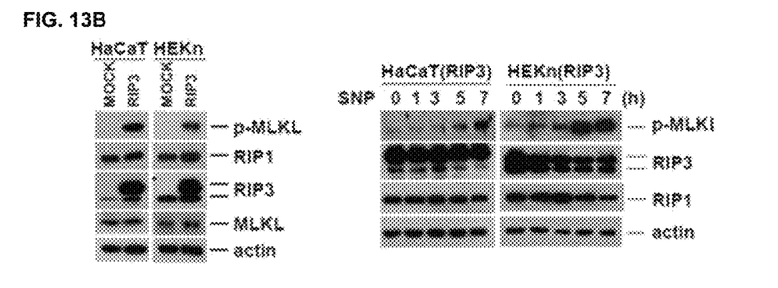
FIG. 13B shows a result confirming MLKL phosphorylation promotion effect by MLKL phosphorylation and further SNP treatment in RIP3 overexpressing cells.
Figure 14:
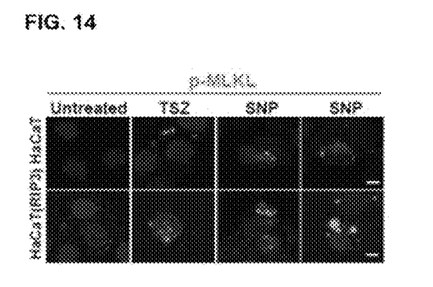
FIG. 14 shows a result confirming p-MLKL localization by SNP treated in early stage using immunochemical staining.

As shown in FIGS. 13A and 13B, in RIP3 knockdown cells, no MLKL phosphorylation was observed, which means that MLKL phosphorylation is dependent on RIP3 (FIG. 13A). Further, in RIP3 overexpressing cells, MLKL phosphorylation was observed without further stimuli such as SNP, and in the case of further treating SNP, MLKL phosphorylation was further promoted (FIG. 13B). In addition, as shown in FIG. 14, in early stage, 3 mM of SNP was treated for 6 hours, and p-MLKL was observed by immunochemical staining. As a result, p-MLKL was seen in punctuate structures before translocation to plasma membrane, which is similar to cells treated with TSZ.

Figure 15A:
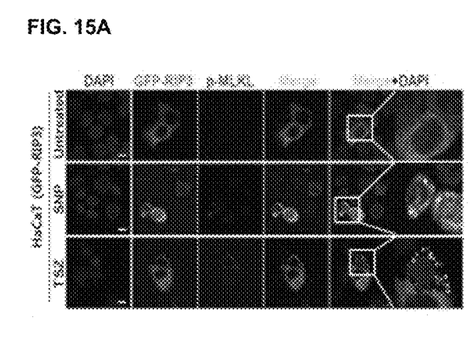
FIGS. 15A and 15B show a result analyzing p-MLKL and RIP3 localizations through fluorescence analysis using antibodies in RIP3-overexpressing HaCaT and HEKn cells.
Figure 15B:
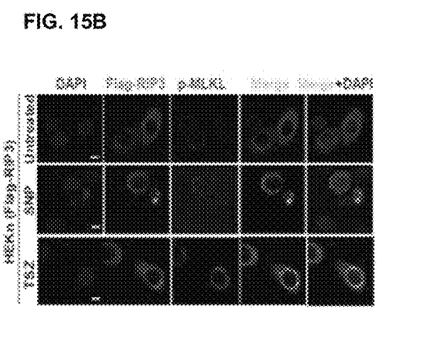

RIP3-overexpressing HEKn cells were treated with TSZ and 5 mM of SNP and stained with p-MLKL or p-MLKL and Flag antibodies to identify its localization. The result is shown in FIGS. 15A and 15B. As shown in FIGS. 15A and 15B, in RIP3-overexpressing HaCaT and HEKn cells treated with SNP, p-MLKL was co-located with RIP3 in early stage punctuate bodies, similar to the pattern seen with TSZ treatment.

This result indicates that elevated levels of phosphorylated MLKL in TEN samples may activate necroptosis, and that the RIP3-MLKL pathway plays an important role in TEN pathology. Further, the result indicates that knockdown of RIP3 and MLKL resulted in inhibition of SNP-induced cell death via necroptosis. It can be understood that SNP not only initiates caspase activation, but also induces programmed necrosis, and that blockage targeting RIP3 or MLKL inhibits SNP-induced skin necroptosis, irrespective of caspase activation.

Example 7. Confirmation on Effect of Inhibition of RIP3-MLKL Pathway on Necroptosis Inhibition From Example 6, it was confirmed that the blockage of the RIP3-MLKL pathway inhibited necrotic cell death. Thus, it was examined whether SNP-induced cell death may be effectively inhibited by treating a substance actually blocking the path. Specifically, the cell death inhibition effect was examined by treating Nec-1, dabrafenib, and NSA.

Figure 16:
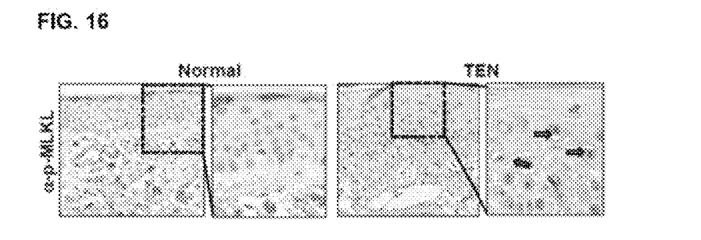
FIG. 16 shows a result confirming an increase in p-MLKL observed in TEN patients' skin.

As shown in FIG. 16, unlike normal skin, in TEN patients' skin, elevated levels of phosphorylated MLKL were detected. In this regard, if an RIP3 inhibitor inhibits elevated levels of phosphorylated MLKL and necroptosis, it may be an effective target for treating TEN patients. In order to confirm this, FIGS. 17A and 17B shows the effect of dabrafenib on MLKL phosphorylation inhibition in RIP3 overexpressing cells.

Figure 17A:
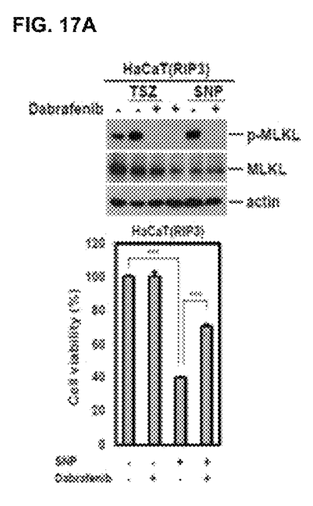
FIGS. 17A and 17B show a result confirming MLKL basal phosphorylation inhibition and SNP-induced p-MLKL inhibition effects (FIG. 17A) and necroptosis inhibition effect (FIG. 17B) in RIP3 overexpressing cells by dabrafenib treatment.
Figure 17B:
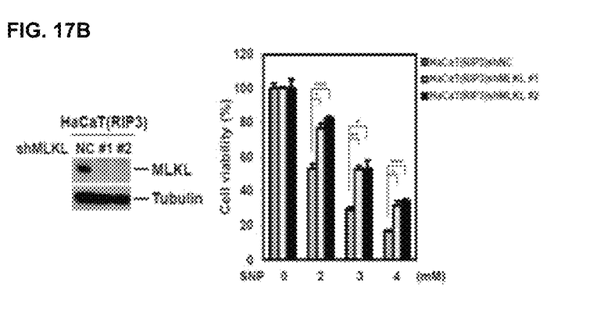

As shown in FIGS. 17A and 17B, the basal phosphorylation of MLKL in RIP3 overexpressing cells, and SNP-induced p-MLKL were eliminated by an RIP3 inhibitor dabrafenib (FIG. 17A). This effect indicates that dabrafenib is capable of inhibiting SNP-induced cell death. Also, knockdown of MLKL in RIP3 HaCaT cells reduced SNP-induced cell death (FIG. 17B), which indicates that activation of MLKL is associated with SNP-mediated cell death. This result demonstrates that the RIP3 inhibitor is capable of effectively inhibiting activation by MLKL phosphorylation abnormally increased in TEN patients, thereby inhibiting cell death via necroptosis in TEN patients, particularly SNP-induced necrosis.

Figure 18:
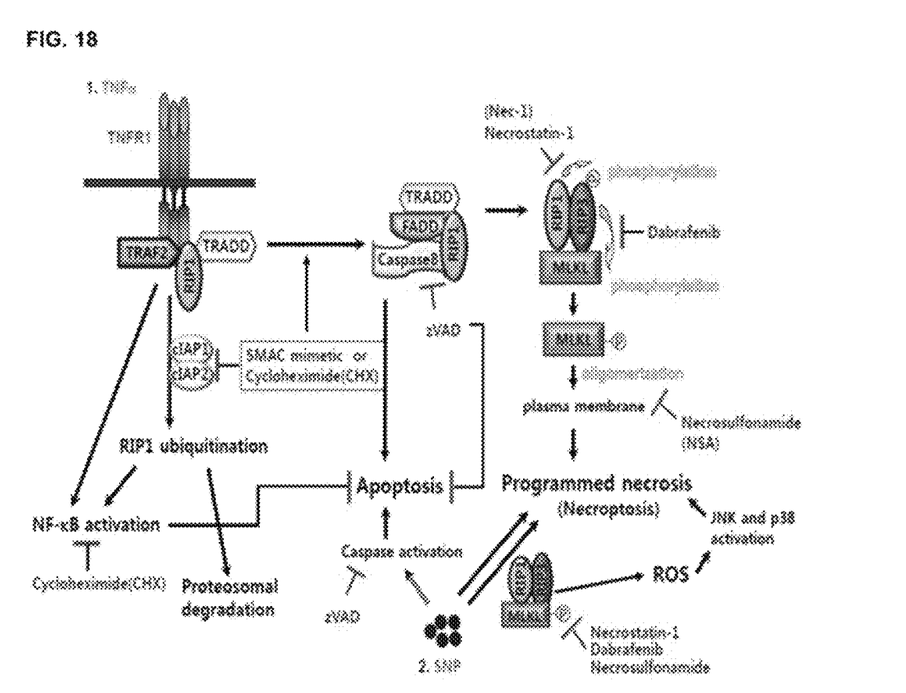
FIG. 18 shows the RIP3-MLKL pathway and necroptosis inhibition mechanism by blocking the pathway.

As confirmed above, necroptosis is capable of being effectively inhibited by blocking the RIP3-MLKL complex pathway, and the pathway may be blocked by blocking or inhibiting RIP3 phosphorylation or inhibiting MLKL phosphorylation. The RIP3-MLKL pathway blockage leads to inhibition of skin necroptosis, thereby effectively preventing or treating skin necroptosis diseases, particularly TEN/SJS. FIG. 18 shows a schematic view of the RIP3-MLKL pathway.

What is claimed is:
1. A method of treating a Stevens-Johnson syndrome/toxic epidermal necrolysis (SJS/TEN) disease, the method comprising:
administering dabrafenib to a subject requiring treatment.
2. The method of claim 1, wherein the dabrafenib is an RIP3 inhibitor.

* * * * *